US008417542B2

(12) United States Patent  (10) Patent No.: US 8,417,542 B2
Lytle et al. (45) Date of Patent: Apr. 9, 2013

(54) GENERATION AND SHARING OF A CUSTOM MODE OF A MEDICAL INSTRUMENT THROUGH A SOCIAL COMMUNITY

(75) Inventors: Larry Lytle, Rapid City, SD (US);
Alf-Kare Eide Riisnaes, Rapid City, SD (US); Kip Lytle, Rapid City, SD (US);
Shawn Gab, Rapid City, SD (US)

(73) Assignee: 2035, Inc., Rapid City, SD (US)

( * ) Notice: Subject to any disclaimer, the term of this patent is extended or adjusted under 35 U.S.C. 154(b) by 377 days.

(21) Appl. No.: 12/626,635

(22) Filed: Nov. 26, 2009

(65) Prior Publication Data

US 2011/0125515 A1   May 26, 2011

(51) Int. Cl.
*G06Q 10/00* (2006.01)
*G06Q 50/00* (2012.01)
(52) U.S. Cl. .............................................. 705/2; 705/3
(58) Field of Classification Search .................. 705/2, 3
See application file for complete search history.

(56) References Cited

U.S. PATENT DOCUMENTS

| 6,527,797 | B1 * | 3/2003 | Masotti et al. .................. 607/89 |
| 2003/0023155 | A1 * | 1/2003 | Tsunoda ....................... 600/407 |
| 2006/0177795 | A1 * | 8/2006 | Sorensen et al. ................ 433/98 |
| 2008/0319575 | A1 * | 12/2008 | Vahlberg et al. .............. 700/232 |
| 2010/0168605 | A1 * | 7/2010 | Aarts ............................ 600/549 |
| 2011/0040546 | A1 * | 2/2011 | Gerber et al. ................... 703/11 |

* cited by examiner

*Primary Examiner* — Neha Patel
(74) *Attorney, Agent, or Firm* — Raj Abhyanker, P.C.

(57) ABSTRACT

A computer-implemented method of a mode server is disclosed. The method includes authenticating a medical instrument based on an identifier associated with the medical instrument using a processor. The method includes authenticating a user of the medical instrument based on a password using the processor. The method also includes generating a graphical representation of the medical instrument, and providing a set of rules associated with the medical instrument based on the identifier and the user. In addition, the method includes generating a custom mode of operation of the medical instrument based on a response of the user and creating a name associated with the custom mode of operation. The method further includes automatically programming the medical instrument based on the custom mode, and sharing the custom mode with other users and other medical instruments based on the set of rules.

3 Claims, 14 Drawing Sheets

| USER 700 | MODES 702 | FRIENDS 704 | ACCESS PRIVILEGE 706 | MEDICAL INSTRUMENT 708 | OTHERS 710 |
|---|---|---|---|---|---|
| BOB | 1, 6, 5 | SANDY, BILL, JOHN | ALL | Q1000 | X, Y |
| SANDY | CUSTOM 1 "ARTHRITICS" | WILLIAM | LIMITED | PROBE | X, M |
| BILL | CUSTOM 3 | NONE | VIEW ONLY | Q10 | A, B |
| ⋯ | ⋯ | ⋯ | ⋯ | ⋯ | ⋯ |

FIGURE 7

GENERATION AND SHARING OF A CUSTOM MODE OF A MEDICAL INSTRUMENT THROUGH A SOCIAL COMMUNITY

FIELD OF TECHNOLOGY

This disclosure relates generally to medical technology and more particularly to generation and sharing of a custom mode of a medical instrument through a social community.

BACKGROUND

A medical instrument (e.g., a low-level laser based medical instrument such as the Q1000® by 2035, Inc.™) may be designed to treat a medical condition (e.g., arthritis, diabetes, fractures) affecting a biological medium. The medical instrument may be designed to operate through a variety of preconfigured modes, where each preconfigured mode defines delivery of laser-light by varying wavelength and/or frequency parameters. The preconfigured modes may be factory set based on empirical studies of biological mediums suffering from the medical condition.

However, the preconfigured modes may not be optimized for a particular mammal. For example, the particular biological medium may have secondary factors (e.g., high blood pressure, skin diseases, etc.) which might reduce the effectiveness of the preconfigured modes when operating the medical instrument. As a result, the medical instrument may not be effective in treating the particular biological medium.

SUMMARY

Several methods and a system for generation and sharing of a custom mode of a medical instrument through a social community are disclosed.

In one aspect, a computer-implemented method of a mode server is disclosed. The method includes authenticating a medical instrument based on an identifier associated with the medical instrument using a processor. Also, the method includes authenticating a user of the medical instrument based on a password using the processor. The method further includes generating a graphical representation of the medical instrument, and providing a set of rules associated with the medical instrument based on the identifier and the user. In addition, the method includes generating a custom mode of operation of the medical instrument based on a response of the user and creating a name associated with the custom mode of operation. The method further includes automatically programming the medical instrument based on the custom mode, and sharing the custom mode with other users and other medical instruments based on a set of rules and a preference of the user.

In another aspect, a computer-implemented method of a client device includes selecting a pulsation power, a pulsation frequency, and a pulsation duration of a medical instrument using a processor. The wavelength of the radiation can be adjusted by using different laser diodes. The method further includes creating a custom mode of operation of the medical instrument when the frequency and the wavelength of a plurality of laser diodes of the medical instrument are selected. In addition, the method includes generating a name of the custom mode of operation, and sharing the custom mode of operation with other client devices through a mode server communicatively coupled with the client device through a network.

In yet another aspect, a system includes an authentication server of a mode server to allocate a parameter to a medical instrument based on a unique identifier of the medical instrument. The system also includes a configuration server of the mode server to associate a light position map and a treatment rule to the medical instrument based on the unique identifier of the medical instrument. In addition, the system includes a network and a client device communicatively coupled to the authentication server, the configuration server, and to the medical instrument to create and share a mode of operation of the medical instrument with other client devices when a user of the medical instrument customizes at least one frequency parameter of the medical instrument consistent with the light position map and the treatment rule. In several embodiments, the medical instrument may be a laser therapy device.

In several embodiments the treatment or therapy administered by the medical instrument to treat a biological medium may be referred to as, but not limited to, low-level laser therapy (LLLT), laser biostimulation, laser irradiation, laser therapy, low-power laser irradiation, or low-power laser therapy. In several embodiments, the medial instrument may provide laser therapy or laser treatment to the biological medium.

The methods and systems disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

Example embodiments are illustrated by way of example and are not a limitation on the figures of the accompanying drawings, in which like references indicate similar elements and in which:

FIG. 7 is a tabular view illustrating a list of users and related custom modes, according to one embodiment.

Other features of the present embodiments will be apparent from the accompanying drawings and from the detailed description that follows.

DETAILED DESCRIPTION

Several methods and a system for generation and sharing of a custom mode of a medical instrument through a social community are disclosed.

Figure 1:
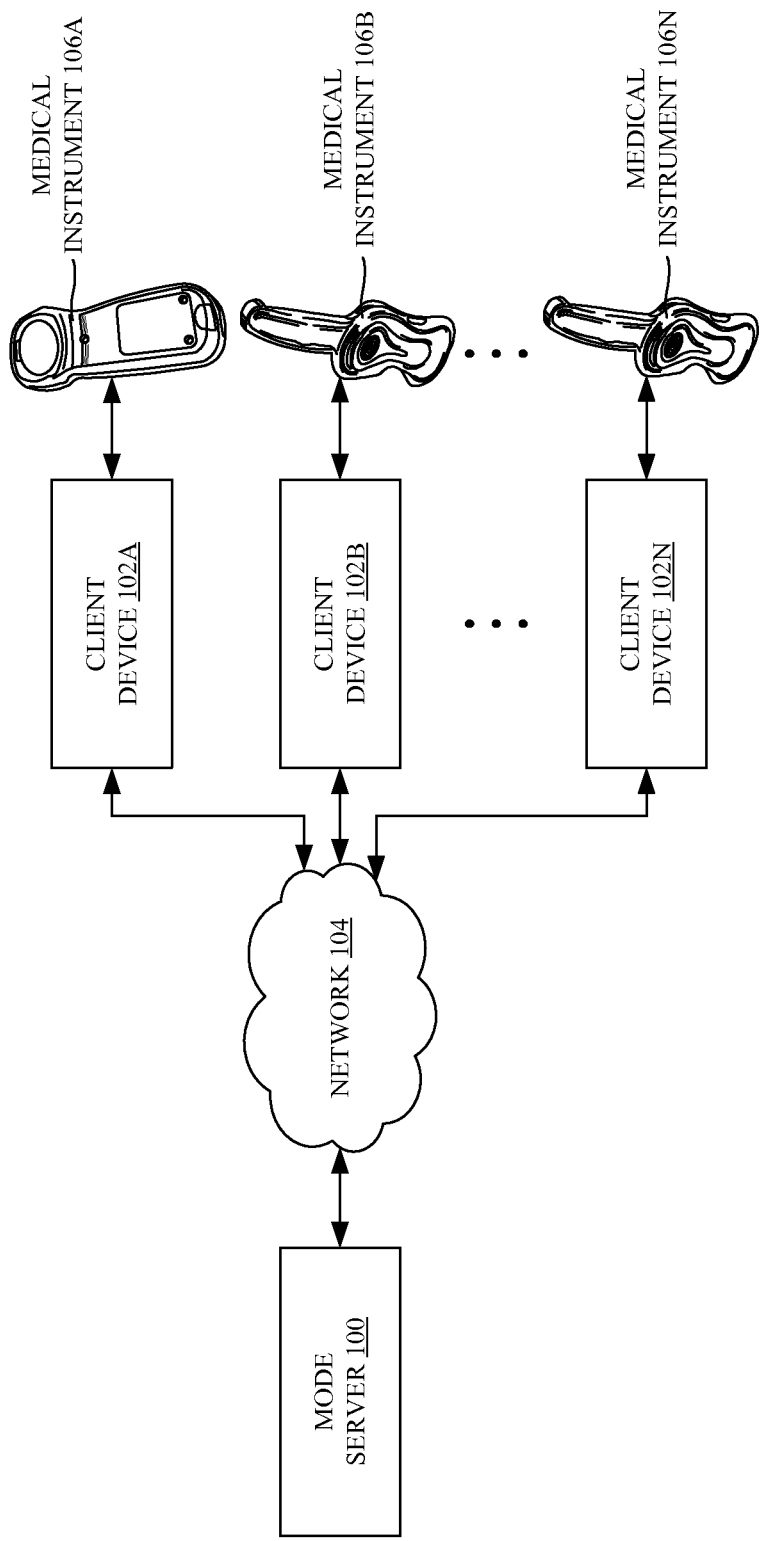
FIG. 1 is a systematic view illustrating a mode server communicating to a client device with a medical instrument through a network, according to one embodiment.

FIG. 1 is a systematic view illustrating a mode server communicating to a client device with a medical instrument through a network. Particularly, FIG. 1 illustrates a mode server 100, a client device 102A-N, a network 104, and a medical instrument 106A-N, according to one embodiment.

The mode server 100 may provide different modes of operation connected to the network 104. The client device 102A-N may be a data processing system. The double headed arrows on the connections shown in FIG. 1 indicate that information may be exchanged in both directions between the network 104 and the client device 102A-N, and between the client device 102A-N and the medical instrument 106A-N. The mode server 100 may be configured to host a custom mode database 226 which provides a central resource for automatically associating a user with other users identified with the other custom modes. The custom mode of operation may provide information for effective medical treatment procedure with the medical instrument 106A-N.

The medical instrument 106A-N (e.g., a low-level laser therapy based medical instrument such as the Q1000® by 2035, Inc.™) may be designed to treat a medical condition (e.g., arthritis, diabetes, fracture) affecting a biological medium. The Q1000® may be a resonating laser with approximately 12 laser diodes, including 8 LEDs with multiple wavelengths (color) of light ranging between 470 nm-940 nm, clustered in a portable hand-held electronic unit. However, in an alternative embodiment, the Q1000® may produce frequencies from 1-20,000 hertz or more. The Q1000® may be designed for treatment of soft tissue application, reduction of inflammation and pain, and re-energizing cells. In alternative embodiments, the medical instrument 106A-N may have a different configuration of laser diodes, LEDs, wavelengths, and frequency ranges.

The medical instrument 106A-N may include standard preconfigured modes of therapy with frequency pulses ranging from 1 to 20,000 Hz. The preconfigured modes may be optimized for treating a particular mammal species with conditions not limited to Acute Tissue Damage, Arthritis Pain and Inflammation, Back Pain, Bone Healing, Burns, Joint Problems, Nerve Damage, Swelling, and Tendon/Ligament Injuries. The medical instrument may be capable of generating 6 or more soliton waves. According to one embodiment, the specification for the medical instrument may include power per diode which may be 5 mW, with the total laser array output of approximately 42 mW, and an area of coverage of approximately 16.4 centimeters squared.

Figure 2:
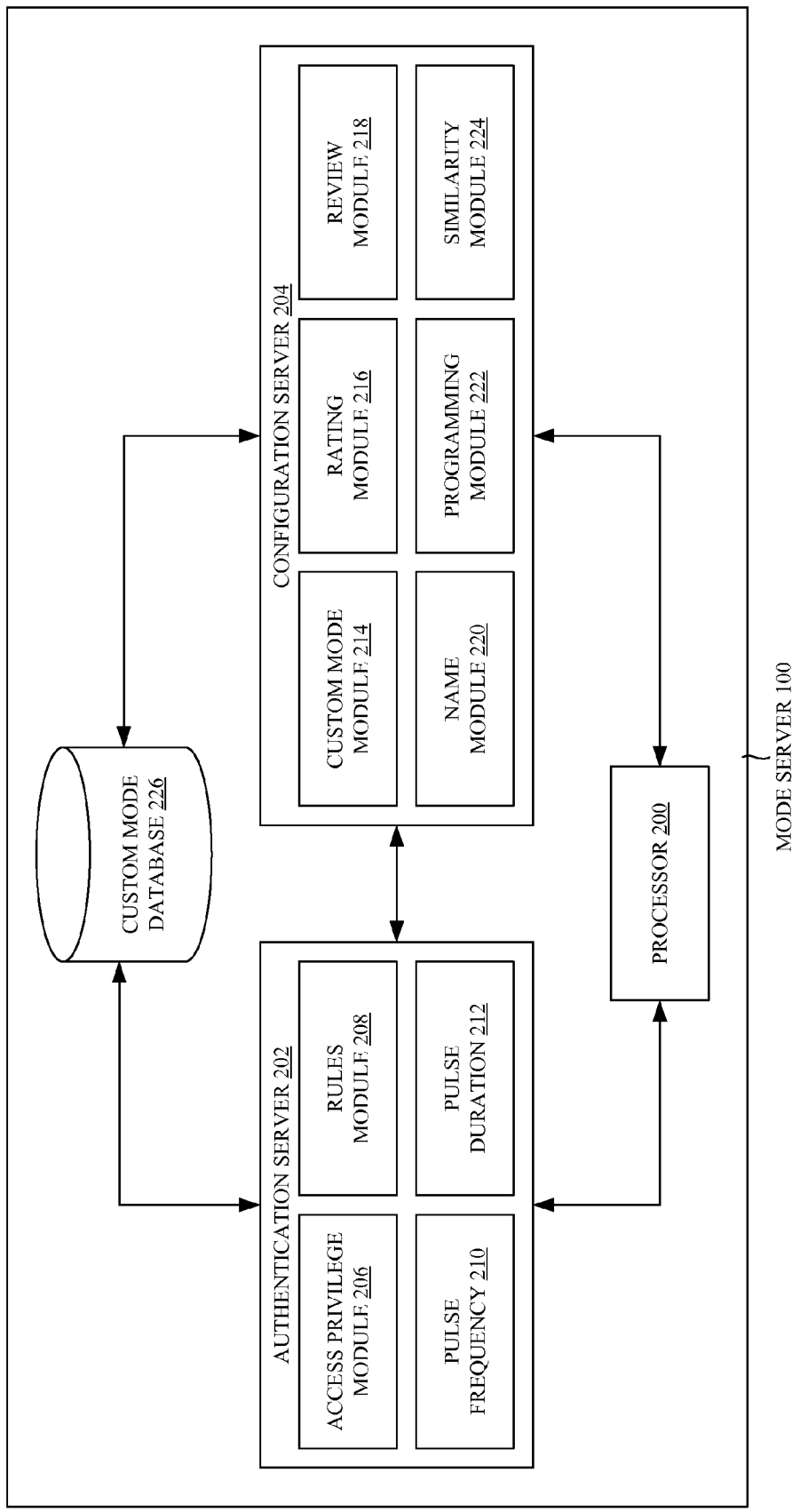
FIG. 2 is an exploded view of a mode server, according to one embodiment.

FIG. 2 is an exploded view of the mode server 100, according to one embodiment. Particularly, FIG. 2 illustrates a mode server 100, a processor 200, an authentication server 202, a configuration server 204, an access privilege module 206, a rules module 208, a pulse frequency 210, a pulse duration 212, a custom mode module 214, a rating module 216, a review module 218, a name module 220, a programming module 222, a similarity module 224, and a custom mode database 226 according to one embodiment.

In the embodiment, the authentication server 202 may include the access privilege module 206, the rules module 208, the pulse frequency 210, and the pulse duration 212. The configuration server 204 may include the custom mode module 214, the rating module 216, the review module 218, the name module 220, the programming module 222, and the similarity module 224. The custom mode database 226 may generate a custom mode of operation of a medical instrument 106A-N based on a response of a user.

The authentication server 202 and the configuration server 204 may be communicatively coupled using a processor 200 to effectively authenticate, generate, create, and share information of the medical instrument 106A-N from the custom mode database 226. The authentication server 202 of the mode server 100 may allocate a parameter to the medical instrument 106A-N. The allocation of the parameter may be based on a unique identifier of the medical instrument 106A-N. The user of the medical instrument 106A-N may be authenticated based on a password using the processor 200. Further, a set of rules may be provided in the rules module 208. The rules module 208 may be associated with the medical instrument 106A-N based on the identifier and the user. The access privilege module 206 may provide sufficient access based on a response of the user. The access to the access privilege module 206 may be authenticated based on a password using the processor 200. The pulse frequency 210 and the pulse duration 212 of a laser diode(s) 302 of the medical instrument 106A-N may be selected using the processor 200. The duration of the pulse may be selected such that the frequency pulsates.

The set of rules indicated in the rules module 208 may be configured in the medical instrument 106A-N for the range of frequency and range of wavelength based on a biological medium. The information may include preconfigured modes of the medical instrument 106A-N. The preconfigured modes may be factory set based on empirical studies of mammals conducted suffering from medical conditions. The information developed may be effective in treating the particular mammal species by automatically associating the user with the other users in a social community described in FIG. 5, according to one embodiment.

The configuration server 204 of the mode server 100 may associate a light position map and a treatment rule to the medical instrument 106A-N. The user may be associated with the custom mode of operation in the custom mode module 214. The user may create a name in the name module 220. The medical instrument 106A-N may be automatically programmed in the programming module 222 based on the custom mode module 214. The custom mode module 214 may provide a rating score in the rating module 216, a feedback score, and a review in the review module 218. The similarity module 224 may provide the sharing of the custom mode with other users and other medical instruments based on the set of rules in the rules module 208 and a preference of the user in a social community. The users may provide information to share the effectiveness of a medical treatment procedure using the custom mode in the custom mode database 226.

Figure 3:
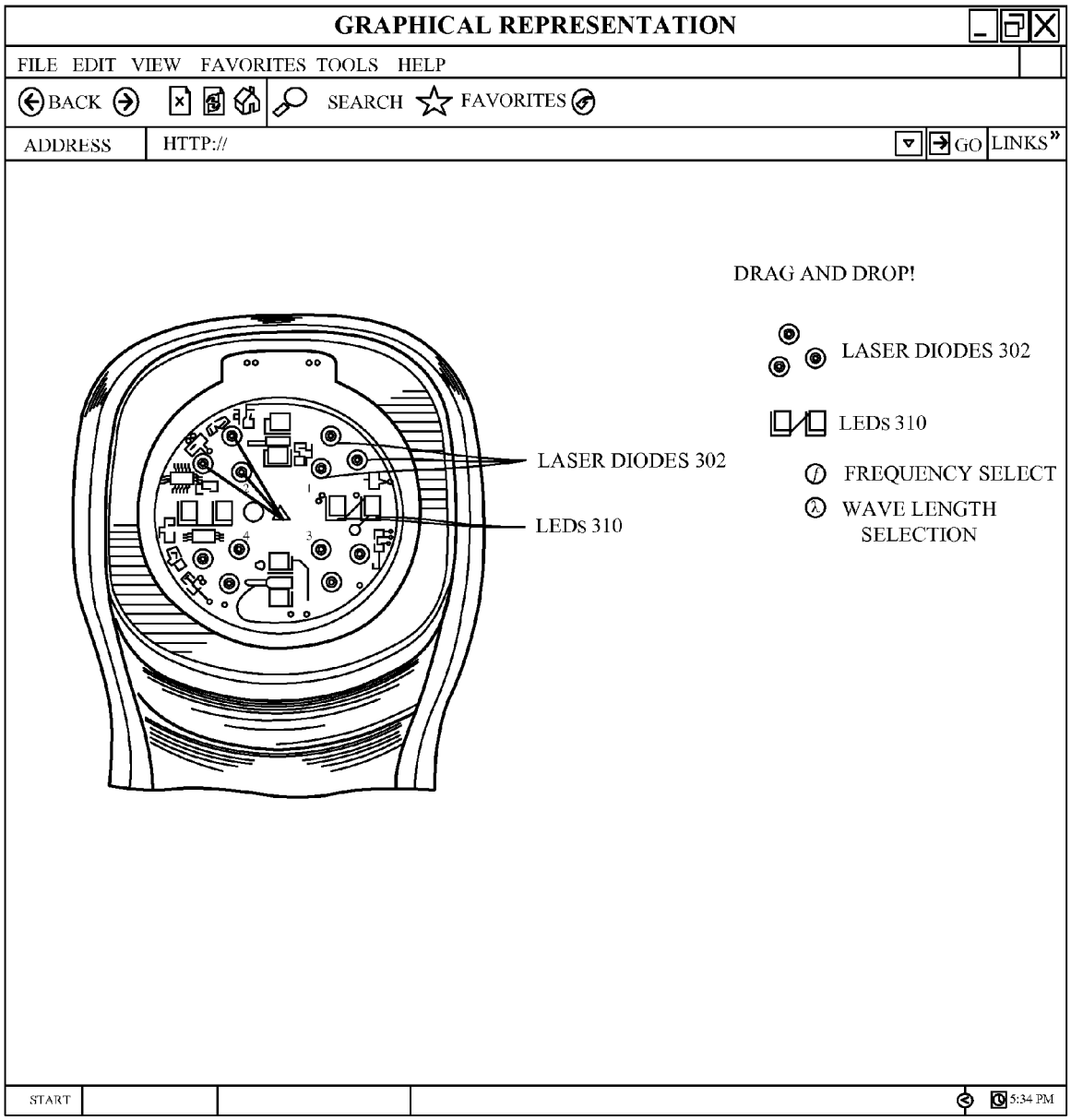
FIG. 3 is a graphical representation of a medical instrument, according to one embodiment.

FIG. 3 is a graphical representation of a medical instrument 350. Particularly, FIG. 3 illustrates a set of laser diodes 302, and a set of Light Emitting Diodes (LEDs) 310.

A p-n junction which emits light when forward biased is known as a Light Emitting Diode (LED). The emitted light may be in the visible or invisible region of the electromagnetic spectrum. The semiconductors used for the manufacturing of LEDs may not be limited to gallium arsenide, and gallium arsenide phosphide. Silicon and germanium are not used for the manufacturing of LEDs because these are primarily heat producing semiconductors and are very poor emitters of light.

The p-n junction has a window at the top of the surface through which light is radiated outside the junction. The amount of light emitted is directly proportional to the forward current. When the light emitting diode is forward biased, the electrons and holes move towards the junction and recombine. After recombination, the electrons in the conduction bands of a n-region fall into the holes lying in the valence band of a p-region. The difference in energy between conduction band and valence band is then radiated in the form of light energy. In ordinary semiconductor diodes this energy difference is radiated as heat energy.

The set of LEDs 310 may radiate light in different colors such as Red, Yellow, Green, Blue, Orange, etc. Some LEDs may even radiate infrared radiation. The color of the emitted light depends on the type of semiconductor used for the diode.

For example, gallium arsenide radiates infrared radiation, gallium arsenide phosphide radiates red or yellow light, gallium phosphide radiates red or green light, and gallium nitride radiates blue light. LEDs which emit one color when forward biased and another color when reverse biased are known as multicolor LEDs. The LEDs may operate at low voltages (e.g., 1.5V to 2.5V). They have very long life of about 10,000 hours and beyond in exceptional cases. They can be switched ON or OFF very fast (approximately equal to 1 nanosecond). The wavelength of the light emitted and the color may depend on the band gap energy of the materials forming the p-n junction The materials used for the LED may have a direct band gap with energies corresponding to near-infrared, visible, and/or near-ultraviolet light A laser diode is a device that produces coherent radiation in the visible or infrared spectrum when the current flows through it. New materials such as indium and phosphorous may be used for the construction of laser diodes which result in greater efficiency. A laser diode consists of a flat junction of two pieces of semiconductors doped very heavily. The p-n junction is separated by a thin active layer. The sides of the laser diode form mirrors of the cavity. A forward bias applied to the p-n junction creates the optical pumping action and the lasing action starts. The laser beam is sent in two opposite directions. When the current flow through the junction is high, a sharp output is obtained. This is the main laser output of the device. The output may be almost monochromatic radiation superposed on a relatively weak radiation background. The laser diode produces a highly directional and monochromatic light beam.

The set of laser diodes 302 may provide radiation in the regions of Red, Green, Blue, Violet, and infrared. They give radiation which may be elliptical and/or wedge shaped. They have outputs in the range of 0.1 mW to 1 W. The laser diodes may be very sensitive to temperature variations. When the temperature changes, wavelength of the emitted light also changes. Relative radiant density also changes due to temperature variation. The laser diodes are available in different shapes and sizes. The sizes depend on the function and power output. When the junction is forward biased, current flows through the junction and laser light is emitted from the junction. However, the power output of laser light is limited. The laser diodes may be smaller in size and have dimensions of 0.1 mm×0.1 mm×0.3 mm. The laser diodes may weigh a fraction of a gram, making them ideal for use in a portable hand-held electronic unit.

The medical treatment procedure may be used successfully for the treatment of traumatic, inflammatory and overuse injuries, pain relief and healing of arthritic lesions, reduction of abscesses, and treatment of persistent non-healing wounds such as cold sores and ulcers. The method of a medical treatment procedure using the medical instrument 106A-N may be used to prevent and/or minimize keloid formation and adhesions, to reduce edema, and to reduce pain from surgical and other treatments. The use of low-level laser based medical instrument such as the Q1000® by 2035, Inc.™ may also encourage the formation of collagen and cartilage in damaged joints and the repair of tendons and ligaments. In addition, the laser light can be used to stimulate acupuncture points in a non-invasive, pain-free manner. The Q1000® may be powered by an intelligent lithium-ion battery delivering multiple wavelengths, power settings, and time intervals via its unique soliton wave technology, ensuring that the healing light penetrates gently into the tissues where it is needed for effective treatment of the particular biological medium.

Figure 4:
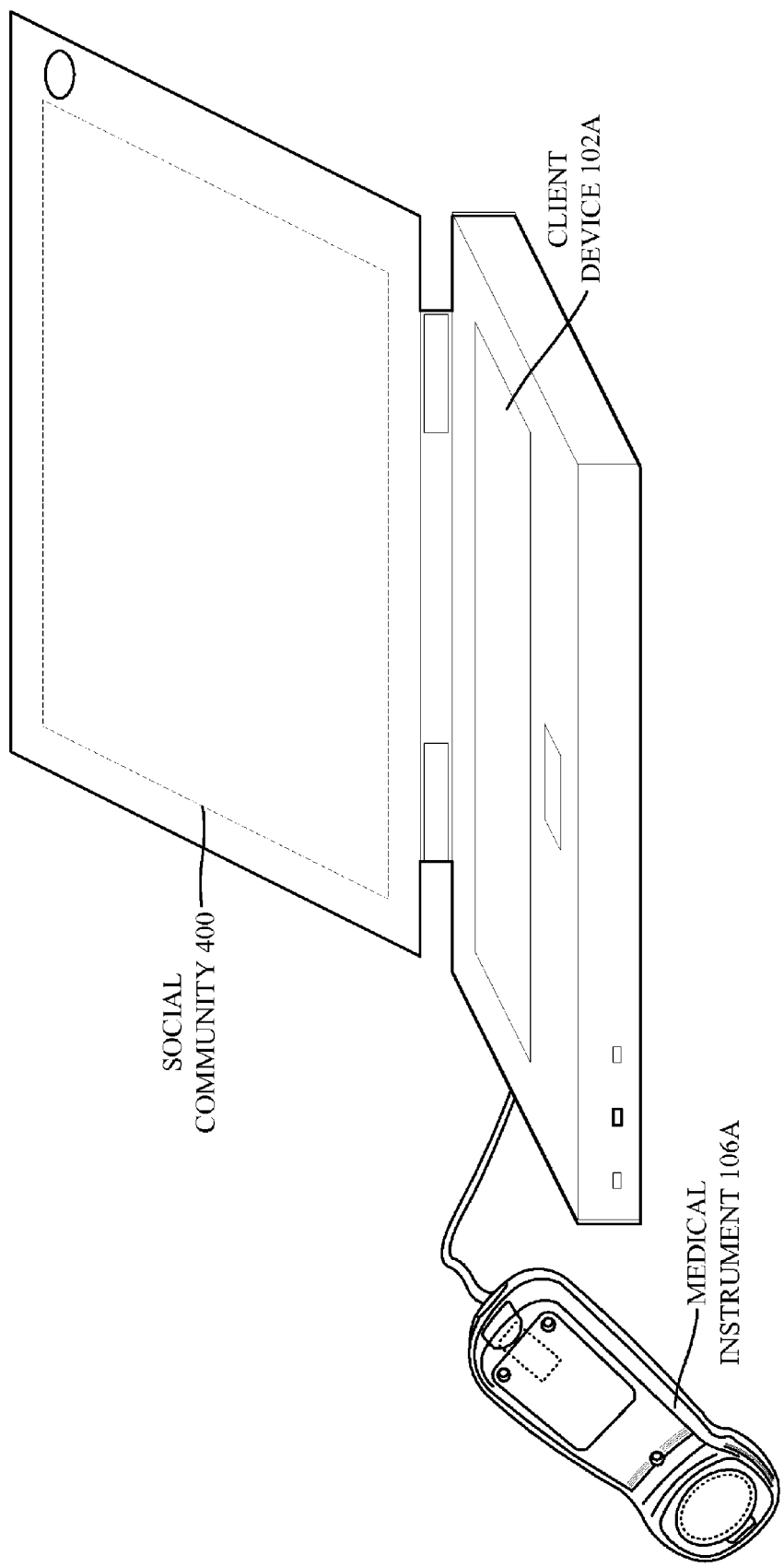
FIG. 4 is a system view of the medical instrument communicatively coupled to the client device, according to one embodiment.

FIG. 4 is a system view of the medical instrument 106A communicatively coupled to the client device 102A, according to one embodiment. Particularly, FIG. 4 illustrates the client device 102A, the medical instrument 106A, and a social community interface 400.

In an example embodiment, the client device 102A (e.g., a computer) may be a data processing system connected to a social community environment through a network (e.g., internet). The social community 400 may provide information related to the effective medical treatment with the medical instrument 106A. In addition, the social community 400 may enable communication with doctors, specialists, and a server that provides valuable information and tips for the user. However, the primary reason for the medical instrument 106A coupled to the client interface 102A is to download modes for treatment. The modes may be downloaded from the social community environment on recommendation from doctors or specialists. In addition, the client device 102A may be communicatively coupled to the authentication server 202, the configuration server 204, and to the medical instrument 106A to create and share a mode of operation of the medical instrument 106A.

Figure 5:
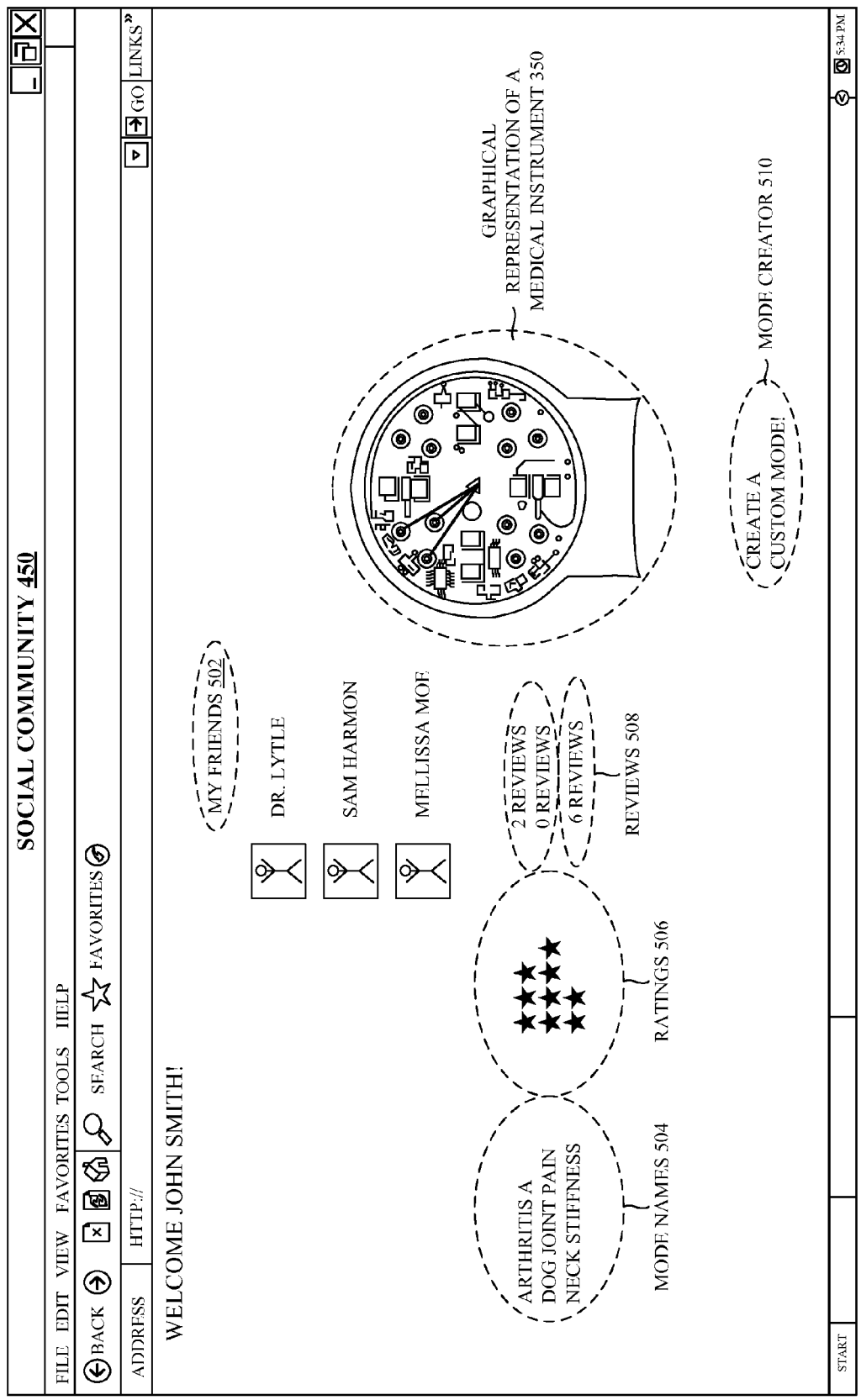
FIG. 5 is a user interface view illustrating a web page of a social community, according to one embodiment.

FIG. 5 is a user interface view illustrating one of a user interface of a social community, according to one embodiment. The user interface may be accessed by a user of a social community 450. A list of "My Friends" 502 may illustrate the list of friends of the user that are connected through the social community 450. The mode names 504 may include a variety of medical conditions (e.g., arthritis, dog joint pain, neck stiffness) affecting a biological medium. The ratings 506 illustrated may provide other users to view the reviews 508. A mode creator 510 may create a custom mode based on a response of the user. The graphical representation of the medical instrument 350 may be generated for sharing the custom mode based on the set of rules and a preference of the user. The user may automatically be associated with other users of the social community 450 based on similarities identified. The similarities between the users of the social community 450 may include a profile data and a preference data. The profile data and the preference data correspond to the ratings 506 and reviews 508 available to the mode creator 510. The custom mode may provide information in effective treatment of the particular mammal.

For example, the web page of the social community 450 may be the homepage of the user. The user may have an animal such as a horse suffering from a joint pain. The user may share his views with other users connected to the friend list. The user may create a custom mode for the treatment of the horse. Further, the user may provide ratings 506 and reviews 508 for the effective treatment using the medical instrument 106A-N.

Figure 6:
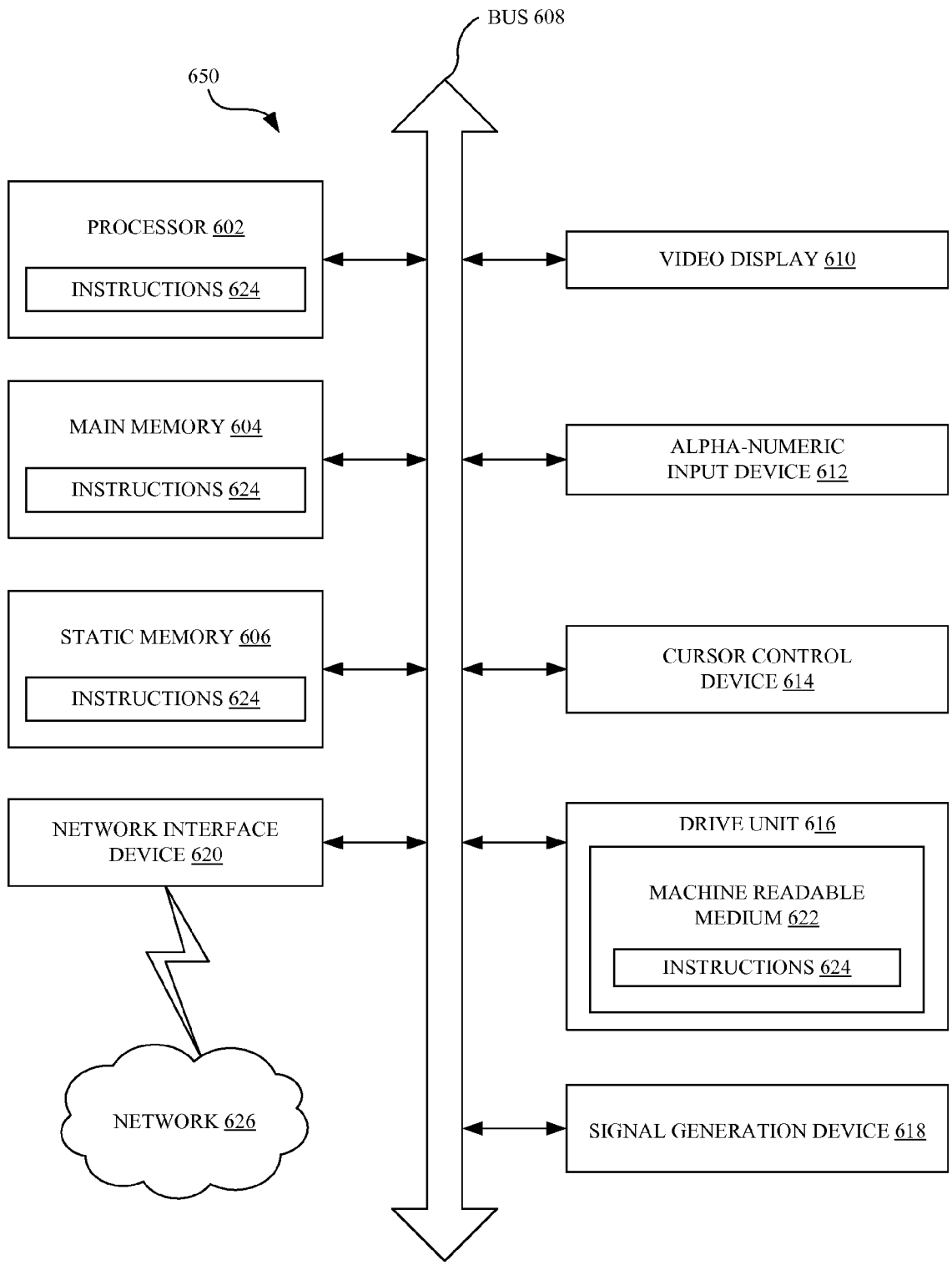
FIG. 6 is a diagrammatic system view of a data processing system in which any of the embodiments disclosed herein may be performed, according to one embodiment.

FIG. 6 is a diagrammatic system view of a data processing system in which any of the embodiments disclosed herein may be performed, according to one embodiment. Particularly, the diagrammatic system view 650 of FIG. 6 illustrates a processor 602, a main memory 604, a static memory 606, a bus 608, a video display 610, an alpha-numeric input device 612, a cursor control device 614, a drive unit 616, a signal generation device 618, a network interface device 620, a machine readable medium 622, instructions 624, and a network 626, according to one embodiment.

The diagrammatic system view 650 may indicate a personal computer and/or the data processing system in which one or more operations disclosed herein are performed. The processor 602 may be a microprocessor, a state machine, an application specific integrated circuit, a field programmable gate array, etc. The main memory 604 may be a dynamic random access memory and/or a primary memory of a computer system.

The static memory 606 may be a hard drive, a flash drive, and/or other memory information associated with the data processing system. The bus 608 may be an interconnection between various circuits and/or structures of the data processing system. The video display 610 may provide graphical representation of information on the data processing system. The alpha-numeric input device 612 may be a keypad, a keyboard, and/or any other input device of text (e.g., a special device to aid the physically handicapped).

The cursor control device 614 may be a pointing device such as a mouse. The drive unit 616 may be the hard drive, a storage system, and/or other longer term storage subsystem. The signal generation device 618 may be a bios and/or a functional operating system of the data processing system. The network interface device 620 may be a device that performs interface functions such as code conversion, protocol conversion, and/or buffering required for communication to and from the network 626. The machine readable medium 622 may provide instructions on which any of the methods disclosed herein may be performed. The instructions 624 may provide a source code or a data code to the processor 602 to enable any one or more of the operations disclosed herein.

FIG. 7 is a tabular view illustrating a list of users and related custom modes, according to one embodiment. In an example embodiment, the table illustrates columns that may include a user field 700, modes field 702, friends' field 704, an access privilege field 706, a medical instrument field 708, and other parameters field 710. The column identified by the user field 700 may include other users of the social community 450 with a group of friends 704. The column modes field 702 may exemplify the different modes associated with the user field 700 such as Bob, Sandy, and Bill. For example, one of the modes 702 may be Custom 1 "Arthritics" for Sandy. Further, the column including a group of friends' fields 704 may share a rating score, a feedback score, and a review of the custom mode to provide information as to effectiveness of a medical treatment procedure.

The column access privilege field 706 may encompass a user having all, limited, and view only privileges based on a password using a processor 200. The medical instrument field 708 may be configured for different pulse frequency 210 and pulse duration 212 for the user field 700. The column medical instrument field 708 may illustrate devices such as Q1000®, a probe device, and Q10®. For devices such as the Q1000®, a probe device may be communicatively coupled to a network for obtaining mode information from the social community 450. However, the device Q10® cannot be coupled to the network for downloading mode information. The other parameter field 710 may include additional custom modes of operation based on the set of rules in the rules module 208 and a preference of the user.

Figure 8:
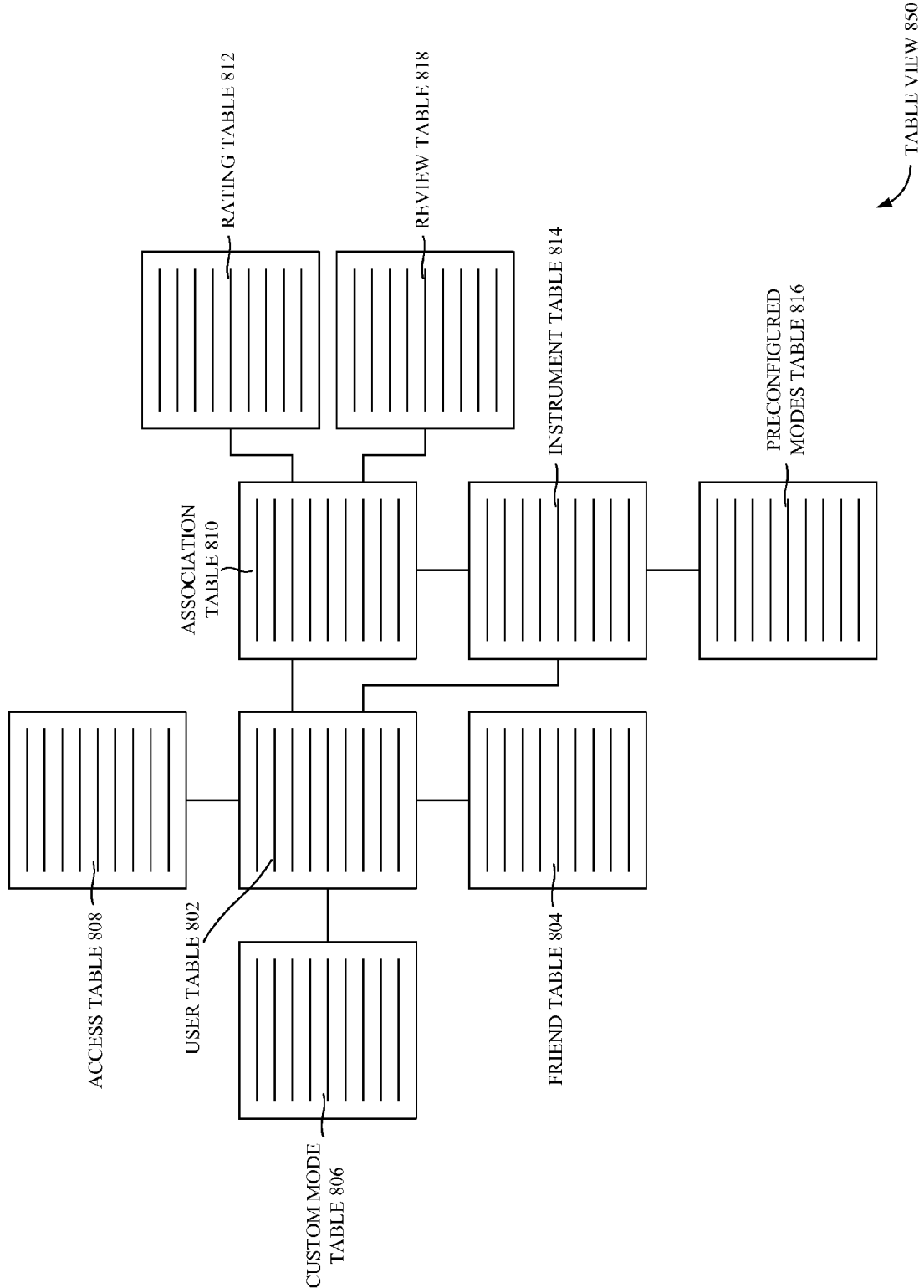
FIG. 8 is a table view illustrating the sharing of custom modes in a social community, according to one embodiment.

FIG. 8 is a table view 850 illustrating the sharing of custom modes in a social community, according to one embodiment. Particularly, FIG. 8 illustrates a user table 802, a friend table 804, a custom mode table 806, an access table 808, an association table 810, a rating table 812, an instrument table 814, a preconfigured modes table 816, and a review table 818, according to one embodiment.

In an example embodiment, the user table 802 may provide the user for generating a custom mode of operation of the medical instrument 106A-N. The custom mode of operation may be available in the custom mode table 806. The user may be associated with the other users through the list of friends in the friend table 804. The user may be authenticated based on the password using the processor 200. The authentication of the user may be provided in the access table 808. The association of the user with other users may be shared in the association table 810.

The association table 810 may contain a profile data, a preference data, and a similarity of the custom mode in a social community. The information from the association table 810 may provide effective medical treatment procedure for treating a biological medium. The instrument table 814 may include a set of medical instruments configured to provide a coordinated delivery of laser light and LED light. The medical instruments 106A-N may provide treatment by varying frequency parameters in the preconfigured modes. The preconfigured modes table 816 may have a particular range of frequency for treating the biological medium. The user may create a name associated with the custom mode of operation. Further, the user may be capable of using the medical data created with the aid of the medical instrument 106A-N to provide ratings 506 and reviews 508 in the review table 818. The review table 818 may provide access to other users in the social community 450. The custom mode of operation may be shared with the other client devices through a mode server 100. The mode server 100 may be communicatively coupled with the client device 102A-N through a network 104. Thereby, the user may have the advantage of utilizing the customized information needed to treat the biological medium through a social community 450 platform.

Figure 9A:
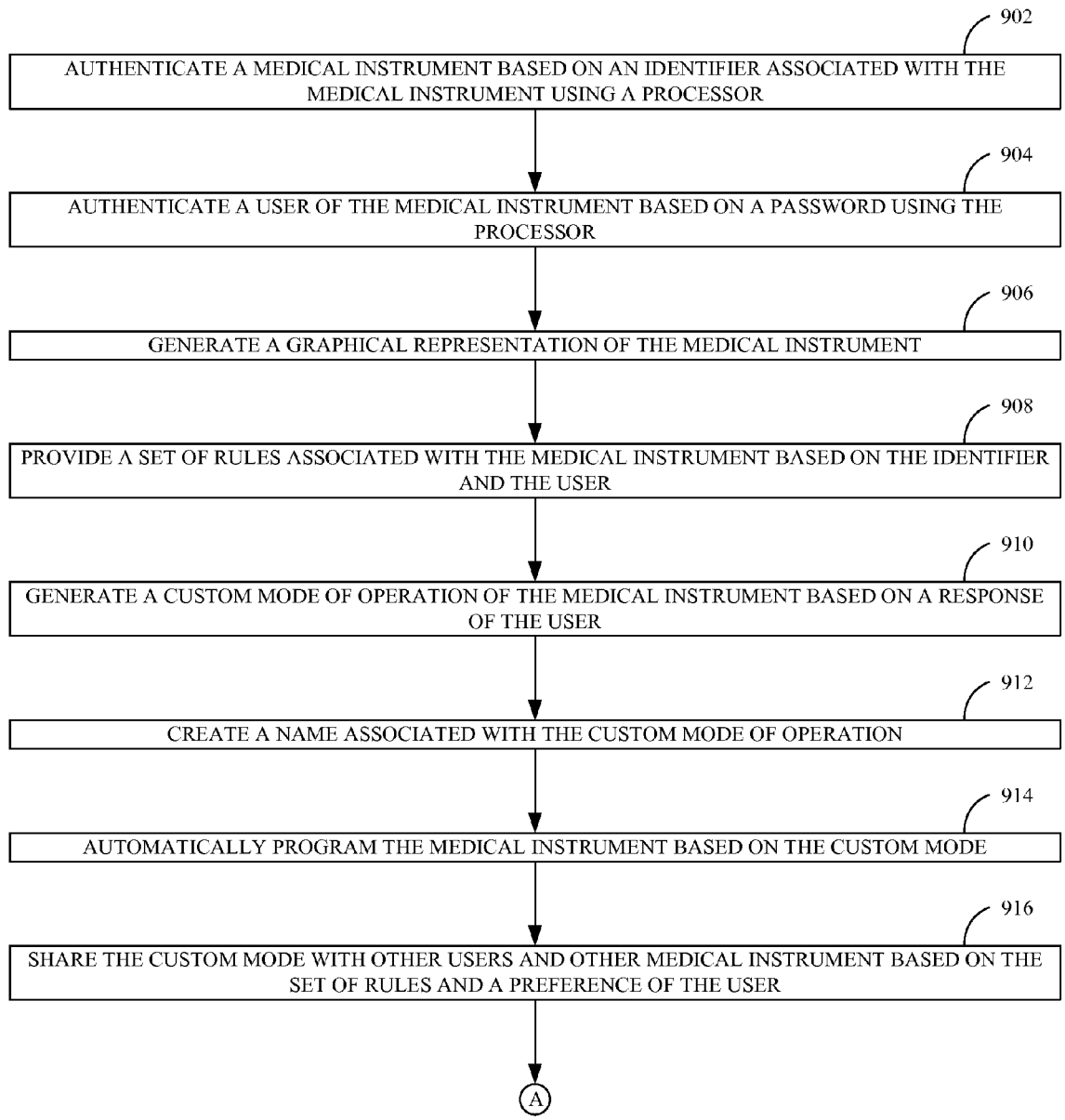
FIG. 9A is a process flow that illustrates generation and share of a custom mode of a medical instrument through a social community, according to one embodiment.

FIG. 9A is a process flow that illustrates generation and share of a custom mode of a medical instrument through a social community. In operation 902, a medical instrument 106A-N based on an identifier is authenticated. The identifier is associated with the medical instrument 106A-N using a processor 200. In operation 904, a user of the medical instrument 106A-N based on a password is authenticated using the processor 200. In operation 906, a graphical representation of the medical instrument 106A-N is generated. In operation 908, a set of rules associated with the medical instrument 106A-N is provided based on the identifier and the user. The set of rules may be provided in the rules module 208. In operation 910, a custom mode of operation of the medical instrument 106A-N is generated based upon a response of the user. In operation 912, a name associated with the custom mode of operation is created. In operation 914, the medical instrument 106A-N is automatically programmed based on the custom mode. The custom mode may be available in the custom mode module 214 of the custom mode database 226. In operation 916, the custom mode with other users and other medical instruments may be shared based on the set of rules and a preference of the user.

Figure 9B:
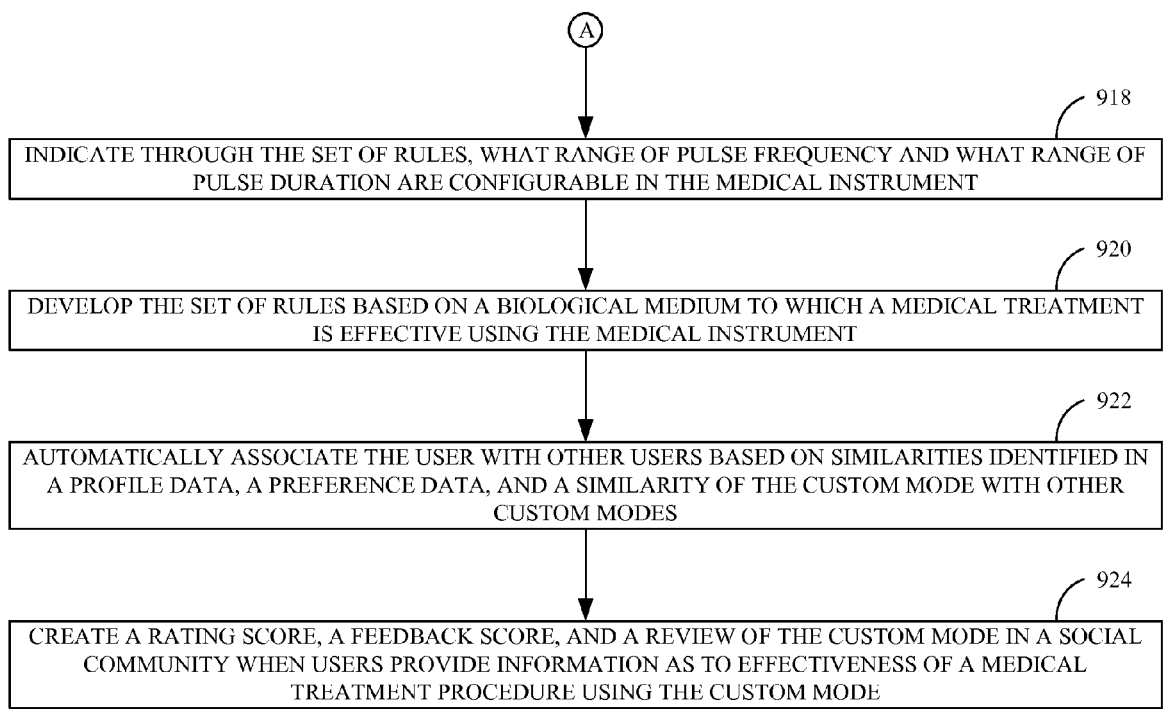
FIG. 9B is a continuation of the process flow illustrated in FIG. 9A showing additional embodiments.

FIG. 9B is a continuation of the process flow illustrated in FIG. 9A showing additional embodiments. In operation 918, the set of rules, range of pulse frequencies 210, and pulse duration 212 configured in the medical instrument 106A-N may be indicated. In operation 920, the set of rules based on a biological medium to which a medical treatment is effective is developed using the medical instrument 106A-N. In operation 922, the user is automatically associated with other users based on similarities identified in one or more of a profile data, a preference data, and a similarity of the custom mode with other custom modes. In operation 924, a rating score, a feedback score, and a review of the custom mode in a social community 450 may be created when users provide information as to effectiveness of a medical treatment procedure using the custom mode.

Figure 10:
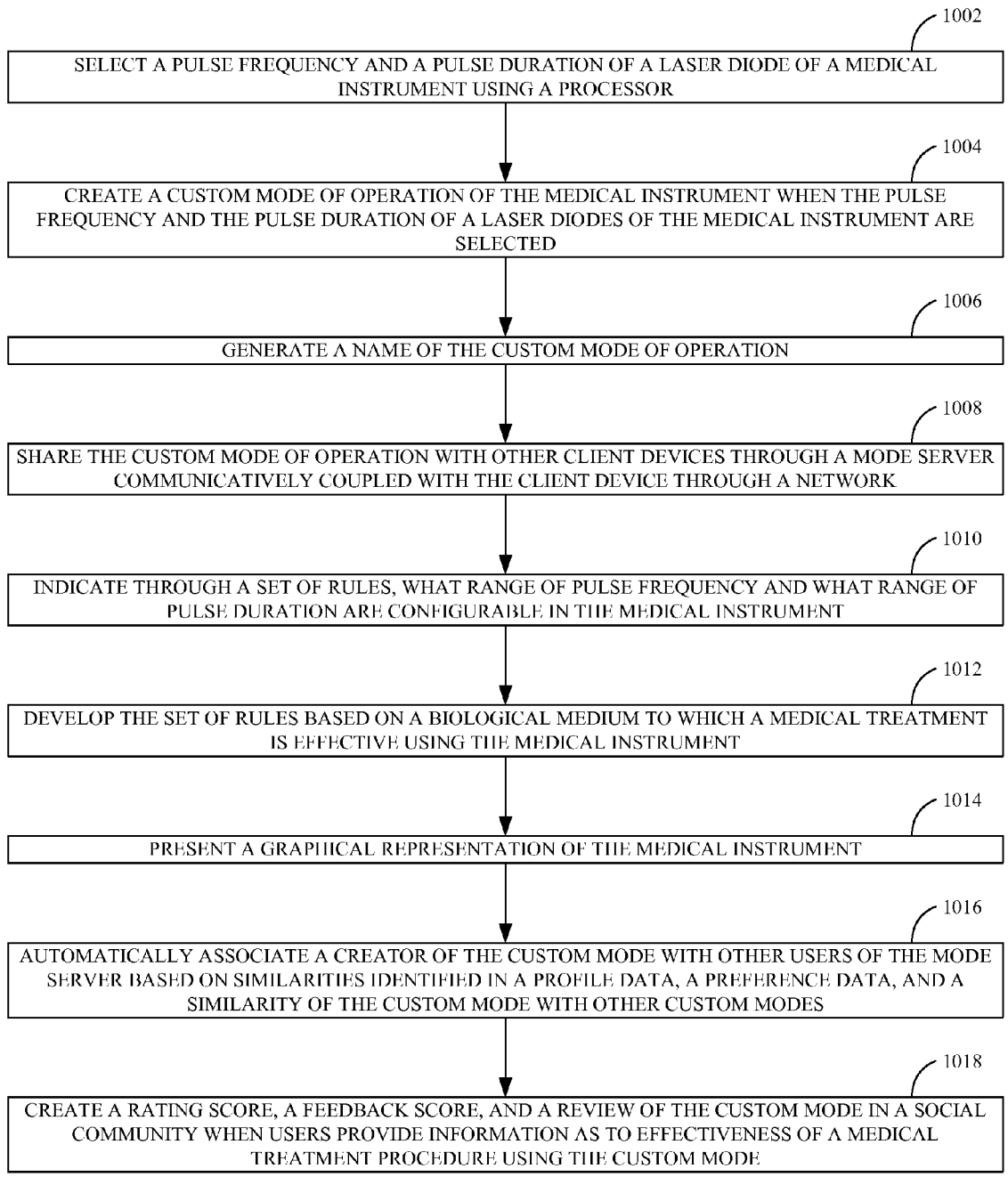
FIG. 10 is a process flow illustrating selection of frequency range and effective medical treatment procedure using the custom mode, according to one embodiment.

FIG. 10 is a process flow illustrating selection of pulse frequency and pulse duration, and effective medical treatment procedure using the custom mode. In operation 1002, a pulse frequency and a pulse duration of a medical instrument 106A-N may be selected using a processor 200. In operation 1004, a custom mode of operation of the medical instrument 106A-N is created when the pulse frequency and the pulse duration of a plurality of laser diodes of the medical instrument are selected. In operation 1006, a name of the custom mode of operation is generated. In operation 1008, the custom mode of operation with other client devices is shared through a mode server 100 communicatively coupled with the client device 102A-N through a network 104. In operation 1010, the set of rules, pulse frequency 210, and pulse duration 212 configured in the medical instrument 106A-N may be indicated.

In operation 1012, the set of rules based on a biological medium is developed to which a medical treatment is effective using the medical instrument 106A-N. In operation 1014, a graphical representation of the medical instrument 106A-N may be presented. In operation 1016, a creator of the custom mode may be automatically associated with other users of the mode server 100, based on similarities identified in one or more of a profile data, a preference data, and a similarity of the custom mode with other custom modes. In operation 1018, a rating score, a feedback score, and a review of the custom mode in a social community may be created when users provide information as to effectiveness of a medical treatment procedure using the custom mode.

Figure 11:
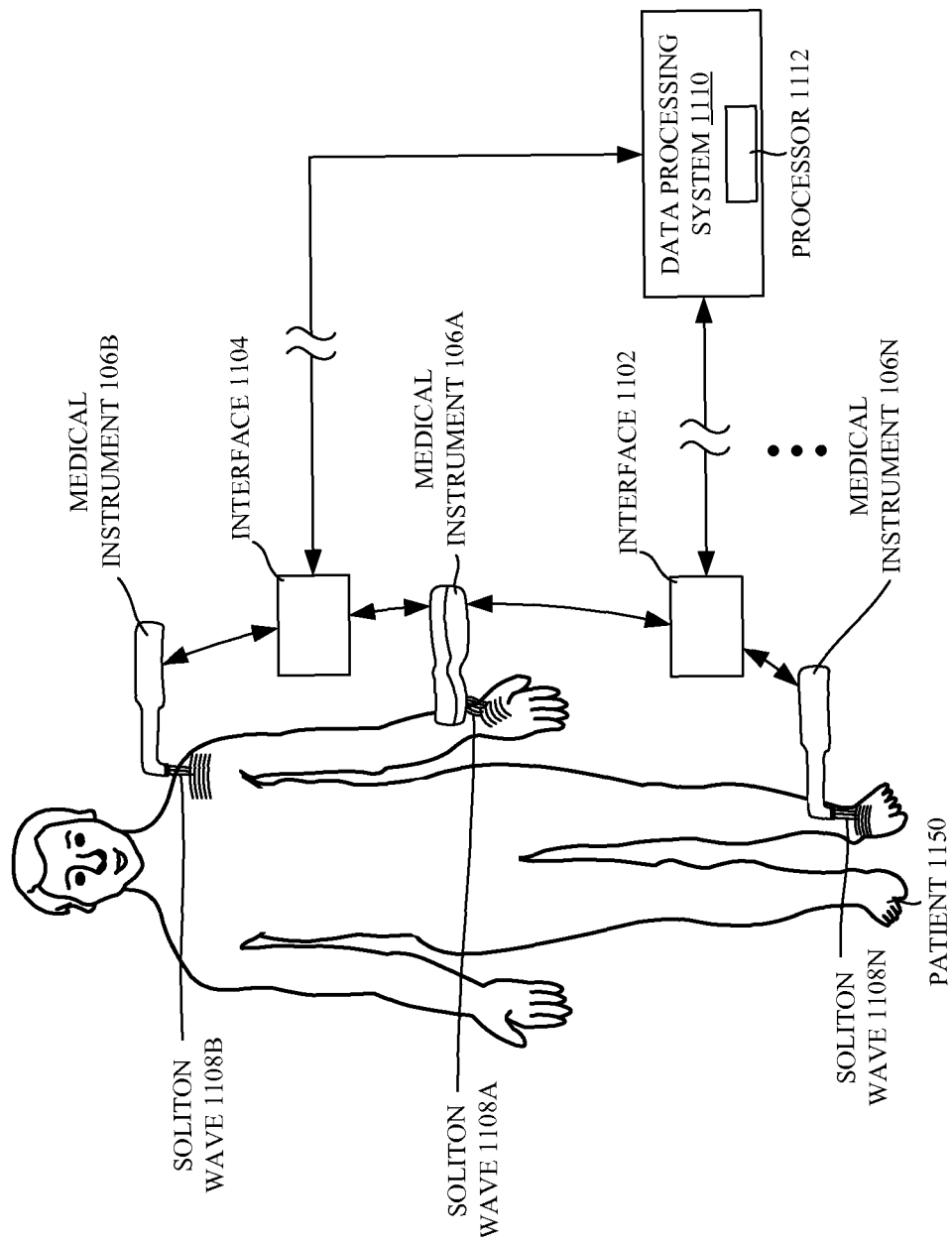
FIG. 11 is a system view that illustrates medical instruments being communicatively coupled and coordinated through a data processing system for treatment of a patient 1150, according to one embodiment.

FIG. 11 is a system view that illustrates medical instruments 106A-N being communicatively coupled and coordinated through a data processing system 1110 for treatment of a patient 1150, according to one embodiment. In particular, FIG. 11 illustrates the medical instruments 106A-N, interfaces 1102-1104, soliton waves 1108A-N, the data processing system 1110, a processor 1112, and the patient 1150, according to one embodiment.

In one or more embodiments, the soliton waves 1108A-N may be generated from the one or more substantially planar laser diode(s). In one or more embodiments, end mirrors of the one or more substantially planar laser diode(s) may be replaced with anti-reflection coatings, and when the one or more substantially planar laser diode(s) are driven, the optical field evolution in the laser diode(s) may be modeled by using two coupled differential equations (example Equations 1 and 2) as:

$$\frac{\partial \psi}{\partial z} = \frac{i}{2}\frac{\partial^2 \psi}{\partial x^2} + (-ihN + (N-1) - \alpha)\psi, \quad (1)$$

and $$D\frac{\partial^2 N}{\partial x^2} = -\pi + N + BN^2 + CN^3 + (N-1)|\psi|^2, \quad (2)$$

where $\psi$ may be the optical field solution, $i=\sqrt{-1}$, x and z the spatial coordinates, h the Henry factor, x the internal loss, N the normalized carrier density $$\left(N = \frac{N'}{N'_{tr}}, N'\right.$$

being the carrier density, and $N'_{er}$ being the transparency carrier density), D the carrier diffusion coefficient, $\pi$ the current pumping coefficient, B the spontaneous recombination coefficient, and C the Auger recombination rate. Here, a linear dependence of the induced refractive index and gain on the carrier density N' may be assumed.

In one or more embodiments, neglecting carrier diffusion in the z direction, and assuming small diffusion, B=0, and C=0, a generalized complex Ginzburg-Landau equation may be obtained from Equations 1 and 2 as example Equation 3:

$$\frac{\partial \psi}{\partial z} = i\left(\frac{1}{2} - i\beta\right)\frac{\partial^2 \psi}{\partial x^2} + \left(\frac{\pi-1}{1+|\psi|^2}(-ih+1) - ih\right)\psi - \alpha\psi, \quad (3)$$

where $\beta$ may account for the transverse carrier diffusion.

In one or more embodiments, soliton wave solutions of the form $\psi(x)e^{i\lambda\epsilon}$ may be numerically obtained. In one or more embodiments, depending on the arrangement of the number of substantially planar laser diodes, constructive interference of the outputs of the number of substantially planar laser diodes may lead to a resultant soliton wave of high amplitude. In one or more embodiments, the resultant soliton wave output may have an amplitude several times higher than a non-soliton wave resultant beam.

In one embodiment, the soliton waves 1108A-N may be generated based on the positioning of the laser diodes. The pattern of the positioning of the laser diodes may affect the production and characteristics of the soliton waves 1108A-N.

The soliton wave 1108A-N is a self-reinforcing solitary wave that maintains its shape while traveling at a constant speed. In an embodiment, the soliton waves 1108A-N may be generated using the medical instruments 106A-N. The medical instruments 106A-N illustrated are portable and handheld devices. The soliton waves 1108A-N may be generated by laser diodes embedded in the medical instruments 106A-N individually or in combination. The generation of soliton waves 1108A-N in combination and coordination may be initiated by using an algorithm that controls the delivery of the soliton wave in the data processing system 1110 that coordinates and controls a delivery of laser and diode light of the medical instruments 106A-N. The algorithm may be generated based on the requirement of a medical procedure.

The medical instruments 106A-N may be communicatively coupled to each other and to the data processing system 1110 through the interfaces 1102-1104. The interfaces 1102-1104 may serve as a communication link between the medical instruments 106A-N. The data processing system 1110 may be a computing device (e.g., computer) that includes the processor 1112 to control the medical instruments 106A-N. The algorithm may be executed by the processor 1112 in the data processing system 1110 to initiate generation of the soliton waves 1108A-N in the medical instruments 106A-N in coordination. The algorithm that controls the delivery of the soliton wave may issue a coordination command to the processor 1112 and the medical instruments 106A-N to generate coordinated soliton waves 1108A-N.

In the example embodiment, the soliton waves 1108A-N are generated by the medical instruments 106A-N individually or in coordination by using the algorithm to coordinate the delivery of the soliton waves 1108A-N. Each of the medical instruments 106A-N may be configured to generate a soliton wave at a particular frequency. In addition, the medical instruments 106A-N may be configured to operate in a particular mode. There may be a variety of operational modes for operating the medical instruments 106A-N in coordination. In one or more embodiments, the operational modes may be based on a prescribed form of a medical treatment. The data processing system 1110 may coordinate and control the medical instruments 106A-N synchronously, asynchronously, or in a pattern. The soliton waves 1108A-N generated, may be delivered on the biological mediums (e.g., such as a part of a body of the patient 1150 that requires treatment) based on a medical procedure for various medical treatments. The medical treatments may include, but are not limited to an arthritic treatment, a diabetic treatment, a skeletal treatment, a muscle treatment, a musculoskeletal treatment, and/or a cardiatric treatment.

In an example embodiment, the soliton waves 1108A-N may be generated by canceling a nonlinear effect and a dispersive effect in a region between an emitting region of the medical instrument 106A-N and the biological medium. The dispersive effect may be a dispersion relationship (e.g., variation of wave propagation with wavelength or frequency of a wave) between a frequency and a speed of the soliton wave 1108A-N.

Figure 12:
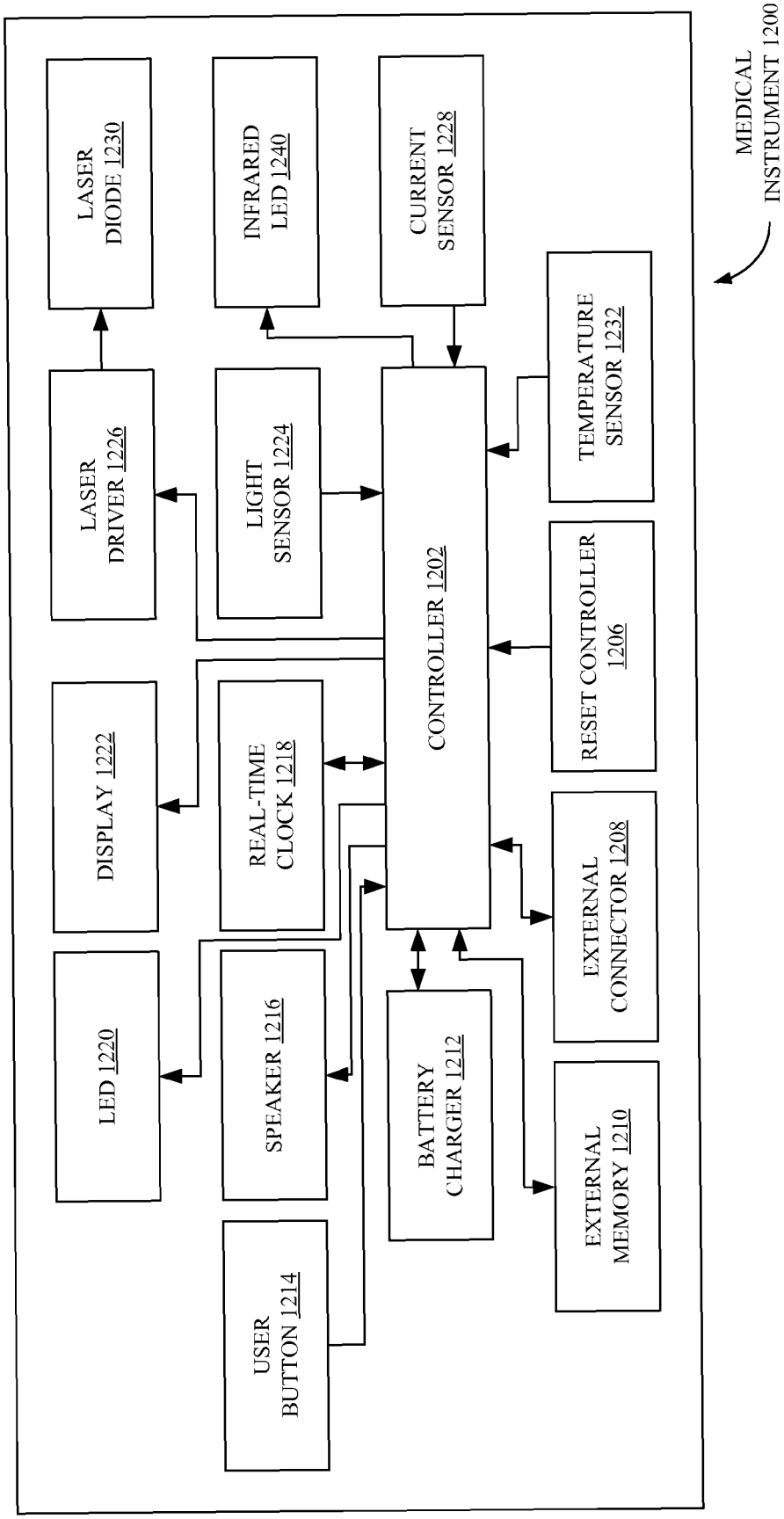
FIG. 12 is a schematic view of a medical instrument, according to one or more embodiments.

FIG. 12 is a schematic view of a medical instrument 1200, according to one or more embodiments. The medical instrument 1200 may in specific describe a schematic representation of the medical instrument 106A. In one or more embodiments, the medical instrument 1200 may include a controller 1202 to control operations fundamental to the working of the medical instrument 1200. In one or more embodiments, the controller 1202 may include a permanent memory (e.g., flash memory) to store firmware associated with controlling the medical instrument 1200. In one or more embodiments, modes of operation may be internally set in the firmware. In one or more embodiments, the controller 1202 is interfaced with a battery charger 1212 to charge a battery (e.g., internal battery) of the medical instrument 1200. In one or more embodiments, the battery charging capability may be provided through an external connector 1208 that may serve purposes not limited to battery charging.

In one or more embodiments, the external connector 1208 may be a multi-pin and multi-use external connector that may also be used to program the internal controller of the medical instrument 1200 (e.g., controller 1202), to calibrate constituent laser diodes 1230, to couple other external compatible devices (e.g. another medical instrument 1200, a probe version of the medical instrument 1200, a computer device, a personal digital assistant (PDA)), and/or to perform diagnostics of the medical instrument 1200.

In one embodiment, the medical instrument 1200 may be powered by a lithium-ion rechargeable battery placed in an inside thereof. Here, the battery charger may plug into the medical instrument 1200 through the external connector 1208, and may closely monitor charge current as well as maximum allowed voltage. In one or more embodiments, the battery may be supplied with a safety circuitry to prevent over-charging/over-discharging of the battery. In one or more embodiments, constituent components of the medical instrument 1200 may be powered during charging of the battery, but user interaction with the medical instrument 1200 may not be possible.

In one or more embodiments, the controller 1202 may be interfaced with an external memory 1210 to enable the medical instrument 1200 to record data indicating a diagnostic requirement of the medical instrument 1200. In one or more embodiments, the recorded data may be useful in enabling servicing of the medical instrument 1200. For example, corrective diagnostics may be performed on the medical instrument 1200 by service personnel following a return of the medical instrument 1200 by a user. In one or more embodiments, the external memory 1210 may be a non-volatile memory such as an Electrically Erasable Programmable Read-Only Memory (EEPROM).

In one or more embodiments, the medical instrument 1200 may be provided with a user button 1214 (shown in FIG. 12 as turning on the controller 1202) to simplify operations thereof. In one embodiment, the user button 1214 may serve as both the power ON/OFF button and the mode selection button.

In one or more embodiments, the medical instrument 1200 may be provided with a speaker 1216 (shown in FIG. 12 as being controlled by the controller 1202) to generate audible alerts as well as indicate the pressing of the user button 1214. In one or more embodiments, the audible alerts may indicate one or more of an operational status of the medical instrument 1200, a beginning of a mode of operation, a beginning of a segment, an end of a mode of operation, and an end of the segment. In one or more embodiments, all audible alerts may be muted by the user during use of the medical instrument 1200.

In one or more embodiments, to enhance serviceability of the medical instrument 1200, a real-time clock 1218 (shown in FIG. 12 as being interfaced with the controller 1202) may be implemented in the medical instrument 1200. In one or more embodiments, data recorded in the external memory 1210 may always be tagged with a current date and time at the time of recording. In one or more embodiments, this may enable a history of use of the medical instrument 1200 to be tracked. For example, when a medical instrument 1200 is returned to the service personnel, the service personnel may be better equipped to understand problems associated with the functioning of the medical instrument 1200.

In one or more embodiments, the medical instrument 1200 may be equipped with one or more LEDs 1220 and a display 1222 (e.g., seven segment display) that serve as user indicators. In FIG. 12, the LEDs 1220 and the display 1222 are shown as being controlled by the controller 1202. In one embodiment, the operational state of the medical instrument 1200 may be indicated with an LED emitting green light that may turn red during a power down. Here, another LED may be provided to indicate battery state and battery charging. For example, if the light emitted by this LED turns yellow during normal operation, it may be indicative of a low power level of the battery. The battery may then need to be charged. The LED may emit red light in a blinking state until charging may be complete, following which the LED may continue to emit green light. In one or more embodiments, the display 1222 may indicate modes that are loaded onto the medical instrument 1200, and, in one embodiment, the modes may be indicated on the display as 0-9. Here, the user may select a mode using the mode selection feature of the user button 1214.

In one or more embodiments, one of the purposes of the controller 1202 may be to control the laser diodes 1230 through laser drivers 1226 thereof. In one or more embodiments, the controller 1202 may control the power level of the laser diodes 1230, and also the flashing of the laser diodes 1230. In addition, in one or more embodiments, the controller 1202 may monitor a light sensor 1224 that measures the ambient light outside the medical instrument 1200. This measurement may be used to control the light intensity of the user indicator LEDs 1220.

In one or more embodiments, the controller 1202 may have the ability to sense the operating current of each laser diode 1230 (see the current sensor 1228 in FIG. 12), which may be used to deactivate laser diodes 1230 that may have failed. In one or more embodiments, this may ensure safety of operation of the medical instrument 1200. In one or more embodiments, current may also be sensed during calibration of the medical instrument 1200 to ensure proper operation of the laser diodes 1230. In one or more embodiments, a power management circuitry of the laser diodes 1230 may be controlled by the controller 1202. In one or more embodiments, infrared light may also be emitted from the infrared LEDs 1240.

In one or more embodiments, the medical instrument 1200 may also include a number of infrared LEDs 1240 (shown as being controlled in FIG. 12 by the controller 1202) to emit infrared light during a duration of a mode of operation. In one or more embodiments, the infrared LEDs 1240 may operate in conjunction with one or more of the visible LEDs 1220.

In one or more embodiments, the controller 1202 may monitor a temperature sensor 1232 to obtain accurate values of the temperatures of the laser diodes 1230. In one or more embodiments, variations of temperature of the laser diodes 1230 may also be tracked.

In one or more embodiments, the medical instrument 1200 may include a reset controller 1206 to monitor a reset button. For example, when a user depresses the reset button and holds the reset button for, say, 5 seconds, the reset controller 1206 may send a reset signal to the controller 1202 to reset the medical instrument 1200. Here, 5 seconds is the threshold time period, and if a user presses the reset button for a time period exceeding the threshold time period, the medical instrument 1200 may be reset.

In one or more embodiments, when the medical instrument 1200 is turned ON and is in an idle state, an LED 1220 indicating power may emit green light. In one or more embodiments, a shut off timer may be started internally to turn the medical instrument 1200 off in case of inactivity (e.g., no further pressing of buttons) for a time period exceeding another threshold time period.

In one or more embodiments, the medical instrument 1200 may be pre-programmed (e.g., by the manufacturer) with several operational modes. In one or more embodiments, the modes may be pre-programmed with the duration of treatment for a therapeutic condition, and the specific frequencies the medical instrument 1200 may be operating at.

In one or more embodiments, where there is a requirement of directed, high-power dosage in a narrow region of a biological medium, the second medical instrument 106B, for example, may be a probe device.

Figure 13:
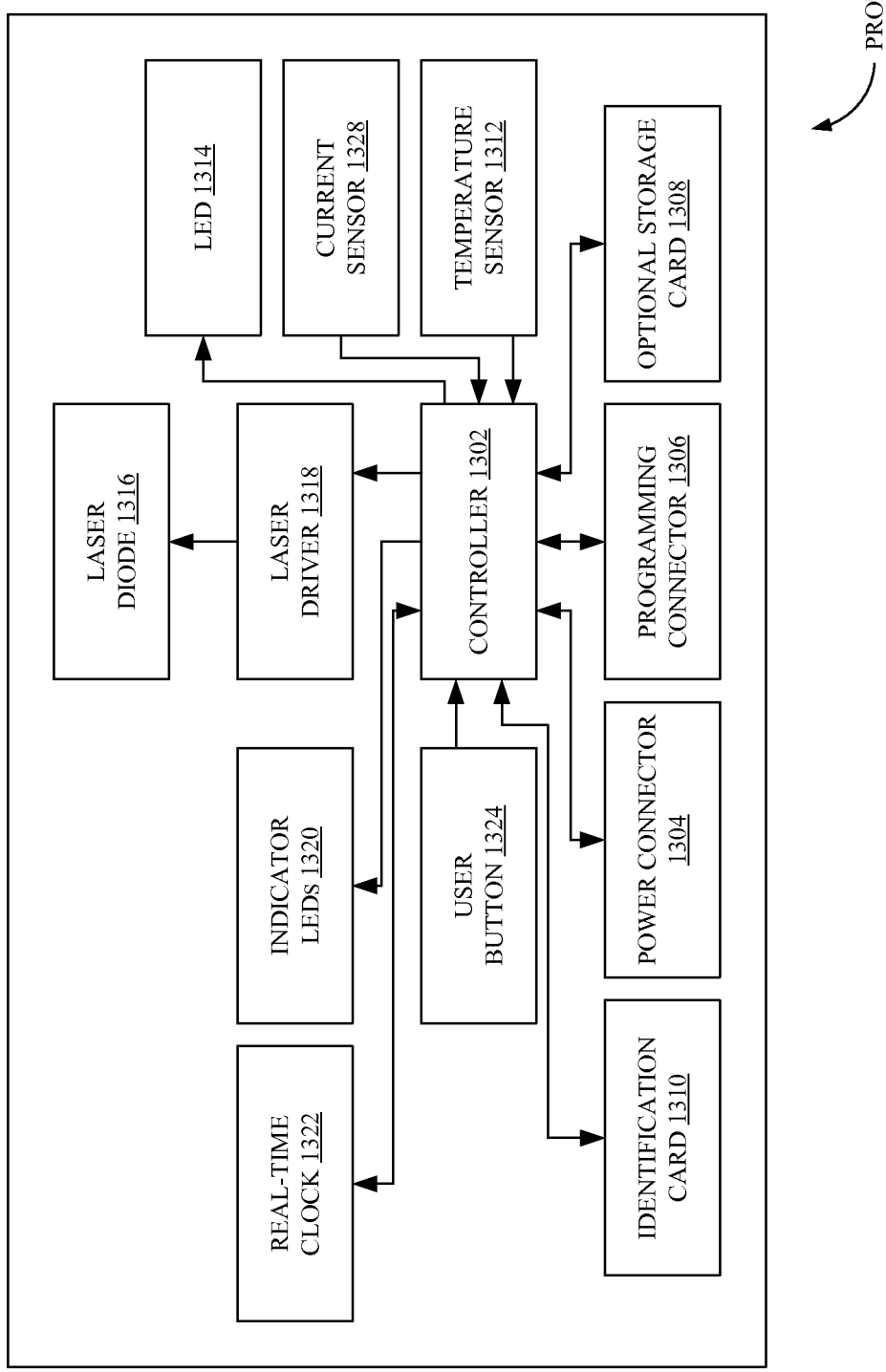
FIG. 13 is a schematic view of a probe device, according to one or more embodiments.

FIG. 13 is a system view of a probe device 1300, according to one or more embodiments. The probe device 1300 described herein may be substantially similar or the same as the medical instrument 106B. In one or more embodiments, the probe device 1300 described herein is a schematic representation of the medical instrument 106B. In one or more embodiments, the probe device 1300 may include a controller 1302 to control all components of the probe device 1300. In one or more embodiments, an operating program of the controller 1302 may be user-upgraded using an optional storage card 1308. In one or more embodiments, the optional storage card 1308 may be a flash card from which different programs may be read.

In one or more embodiments, the probe device 1300 includes a power connector 1304 through which a battery of the probe device 1300 may be charged. In one or more embodiments, a medical instrument 106A may be used to power the probe device 1300 through the power connector 1304. In one or more embodiments, the probe device 1300 may include an identification card 1310. The identification card 1310 may include information regarding types of treatment modes to be activated. The information on the identification card 1310 may be read by controller 1302.

In one or more embodiments, the probe device 1300 may include a programming connector 1306 through which a programming/calibration interface may be provided. In one or more embodiments, the probe device 1300 may be calibrated by a manufacturer and/or serviced by service personnel through the programming connector 1306. In one or more embodiments, a data processing system (e.g., client devices 102A-N) may be coupled to the probe device 1300 through the programming connector 1306. In one or more embodiments, the programming connector 1306 may not be available to a user but only available to the manufacturer and/or service personnel.

In one or more embodiments, an integrated laser driver 1318 may control a laser diode 1316 of the probe device 1300. In one or more embodiments, an operating current of the laser diode 1316 and/or a light output of the laser diode 1316 may be monitored to maintain a constant output of the laser diode 1316. In one or more embodiments, the laser diode 1316 may be calibrated during the manufacturing process and/or the laser driver 1318 may be configured to handle a range of laser diodes.

In one or more embodiments, LEDs (1314, 1320) may be provided to indicate an operational state of the probe device 1300. A light from an LED 1314 may also indicate that the optional storage card 1308 is properly inserted and recognized. In another example, a number of LEDs 1320 may indicate modes selected and/or progress during boot-up. In one or more embodiments, a separate LED 1314 may indicate activity of the laser diode 1316.

In one or more embodiments, in order for corrective diagnostics to be performed by service personnel and/or operating statistics to be obtained by the manufacturer, a real-time clock 1322 may be provided in the probe device 1300. In one or more embodiments, the real-time clock 1322 may be programmed during manufacturing. In one embodiment, power to the real-time clock 1322 may be supplied by a lithium-ion battery of the probe device 1300. In another embodiment, power to the real-time clock 1322 may be supplied by a coin cell battery of the probe device 1300.

In one or more embodiments, the controller 1302 may monitor the current of the laser diode 1316 during operation of the laser diode 1316 through a current sensor 1328. In one embodiment, the current data may be used in the calibration of the probe device 1300.

In one or more embodiments, a temperature sensor 1312 may be provided in the probe device 1300 to monitor a temperature of the laser diode 1316 in order to ensure safety of operation of the probe device 1300.

In one or more embodiments, when the probe device 1300 is powered up, green light may be emitted from an LED 1320. In one embodiment, when the optional storage card 1308 is not present, the green LED 1320 may start to blink to indicate the need to insert the optional storage card 1308. In one or more embodiments, upon insertion of the identification card 1310 and checking for updates residing in the identification card 1310, modes of operation may be downloaded into the probe device 1300. In one or more embodiments, modes of operation present on the identification card 1310 may be loaded.

In one or more embodiments, user selection of modes of operation may be accomplished through a user button 1324. In one or more embodiments, the probe device 1300 may be turned on by a user holding the user button 1324 for a time period exceeding a threshold time period of, say, 5 seconds. In one or more embodiments, a warning LED 1314 may be provided to indicate a state where a laser diode 1316 operating at a wavelength outside the visible spectrum may be used. In one or more embodiments, the probe device 1300 may also be turned off by a user depressing the user button 1324 for a time period exceeding another threshold time period.

In one or more embodiments, if at any point the identification card 1310 is removed, the laser diode 1316 may be turned off, and the probe device 1300 may return to a boot-up state thereof.

In one or more embodiments, one or more substantially planar laser diode(s) of medical instrument 106A may lase at a wavelength of approximately ~650 nm, ~780 nm, or ~808 nm. In one or more embodiments, the medical instrument 106A may operate at a power level of approximately ~42 mW. In one or more embodiments, the probe device 1300 may lase at a wavelength of approximately ~660 nm or ~808 nm. In one or more embodiments, the probe device 1300 may operate at a power level of approximately ~50 mW or ~500 mW. In one or more embodiments, the high power level of the probe device 1300 may provide for deeper penetration into a biological medium (e.g., tissue in a human body).

Although the present embodiments have been described with reference to specific example embodiments, it will be evident that various modifications and changes may be made to these embodiments without departing from the broader spirit and scope of the various embodiments. For example, the various devices, modules, analyzers, generators, etc., described herein may be enabled and operated using hardware circuitry, firmware, software, or any combination of hardware, firmware, or software embodied in a machine-readable medium. For example, the various electrical structures and methods may be embodied using transistors, logic gates, application specific integrated (ASIC) circuitry, or Digital Signal Processor (DSP) circuitry.

In addition, it will be appreciated that the various operations, processes, and methods disclosed herein may be embodied in a machine-readable medium or a machine-accessible medium compatible with a data processing system, and may be performed in any order. Accordingly, the Specification and Drawings are to be regarded in an illustrative manner rather than a restrictive sense.

What is claimed is:

1. A computer-implemented method of a mode server, comprising:
   authenticating, by a computer processor, a laser-based medical instrument based on an identifier associated with the laser-based medical instrument;
   authenticating, by the computer processor, a user of the laser-based medical instrument based on a password;
   generating, by the computer processor, a graphical representation of the laser-based medical instrument;
   providing, by the computer processor, a set of rules associated with the laser-based medical instrument based on the identifier and the user;
   generating, by the computer processor, a custom mode of operation of the laser-based medical instrument based on a response of the user;
   creating a name associated with the custom mode of operation;
   automatically programming, by the computer processor, the laser-based medical instrument based on the custom mode;
   sharing, by the computer processor, the custom mode with other users and other similar laser-based medical instruments based on the set of rules and a preference of the user;
   automatically associating, by the computer processor, the user with other users based on similarities identified in at least one of a profile data, a preference data, and a similarity of the custom mode with other custom modes;
   creating, by the computer processor, at least one of a rating score, a feedback score, and a review of the custom mode in a social community when users provide information as to effectiveness of a medical treatment procedure using the custom mode; and
   indicating, through the set of rules, what range of frequencies and what range of pulse durations are configurable in the laser-based medical instrument,
   wherein the indication is generated using a processor, and wherein the graphical representation of the laser-based medical instrument is a visual representation of a physical region of the medical instrument in which at least one of a laser diode and a light-emitting diode (LED) light are housed,
   wherein the custom mode of operation is a coordinated delivery of laser light and LED light through the laser-based medical instrument, and
   wherein the laser-based medical instrument is a portable hand-held electronic unit that contains laser diodes and LEDs and is configured to varying wavelengths and frequency ranges for the treatment of medical conditions affecting a biological medium.

2. The computer-implemented method of claim 1 further comprising developing the set of rules based on a biological medium to which a medical treatment is effective using the laser-based medical instrument.

3. The computer-implemented method of claim 1 wherein the laser-based medical instrument includes preconfigured modes which are not customizable in addition to the custom mode and other custom modes.

* * * * *